(12) United States Patent
Sobue (10) Patent No.: US 6,706,317 B2
(45) Date of Patent: Mar. 16, 2004

(54) MANUFACTURING METHOD FOR A GAS SENSING ELEMENT (75) Inventor: Shinichiro Sobue, Mie-ken (JP)

(73) Assignee: Denso Corporation (JP)

( * ) Notice: Subject to any disclaimer, the term of this patent is extended or adjusted under 35 U.S.C. 154(b) by 0 days.

(21) Appl. No.: 10/128,317

(22) Filed: Apr. 24, 2002

(65) Prior Publication Data

US 2002/0160104 A1 Oct. 31, 2002

(30) Foreign Application Priority Data

Apr. 26, 2001 (JP) ........................ 2001-130166

(51) Int. Cl.[7] .............................. B05D 5/12; B05D 3/02; B05D 1/36; B05D 3/12
(52) U.S. Cl. .................. 427/58; 427/430.1; 427/376.1; 427/376.2; 427/419.1; 427/240
(58) Field of Search ................. 427/430.1, 58, 427/376.1, 372.2, 419.1, 240; 118/429

(56) References Cited

U.S. PATENT DOCUMENTS

| | | | | |
|---|---|---|---|---|
| 3,910,564 A | * | 10/1975 | Graham et al. | 366/18 |
| 4,380,398 A | * | 4/1983 | Burgess | 366/261 |
| 4,727,929 A | * | 3/1988 | Simmons et al. | 164/516 |
| 5,593,558 A | * | 1/1997 | Sugino et al. | 204/429 |
| 6,042,748 A | * | 3/2000 | Inoue et al. | 252/301.4 S |
| 6,296,704 B1 | * | 10/2001 | Yamazaki | 118/429 |

FOREIGN PATENT DOCUMENTS

| | | | | |
|---|---|---|---|---|
| JP | 9-170999 | | 6/1997 | |
| JP | 2000129496 A | * | 5/2000 | ........... C25D/21/10 |

* cited by examiner

Primary Examiner—Michael Barr
(74) Attorney, Agent, or Firm—Nixon & Vanderhye PC (57) ABSTRACT

A solid electrolytic body is dipped into a slurry stored in a dipping tank, while the slurry is forcibly circulated between the dipping tank and a viscosity adjusting tank by a circulating pump. A slurry film is formed on a predetermined portion of the solid electrolytic body through this dipping treatment. Then, the slurry film is changed into a porous layer through a sintering treatment.

12 Claims, 5 Drawing Sheets

MANUFACTURING METHOD FOR A GAS SENSING ELEMENT

BACKGROUND OF THE INVENTION

The present invention relates to a method for manufacturing a sensing element of a gas sensor. The gas sensor is generally installed in an exhaust gas passage of an internal combustion engine for combustion control or emission control of the internal combustion engine.

A gas sensing element is necessary to control the combustion of an internal combustion engine. The gas sensing element has a cup-shaped solid electrolytic body having a reference gas chamber formed therein. An inside electrode is provided on an inner surface of the solid electrolytic body. An outside electrode is provided on an outer surface of the solid electrolytic body. A porous layer is provided to cover the outside electrode.

When the gas sensing element is manufactured, a solid electrolytic body having a predetermined shape is first prepared. The inside electrode and the outside electrode are respectively provided on the inner and outer surfaces of the solid electrolytic body. Next, the solid electrolytic body is dipped into a slurry to coat a slurry film on the outside electrode. Then, the slurry film is sintered to form the porous layer.

The dipping method of the solid electrolytic body includes a step of dipping the solid electrolytic body into a slurry stored in a dipping tank. To perform the dipping treatment of slurry uniformly and effectively, the dipping tank has large size sufficient for dipping a plurality of solid electrolytic bodies into the slurry at a time. An appropriate jig is prepared to hang the plurality of solid electrolytic bodies so as to be positioned above the dipping tank. The jig is then lowered toward the dipping tank to dip the plurality of solid electrolytic bodies into the slurry stored in the dipping tank.

The dipping tank is equipped with a stirrer provided on the bottom of this dipping tank. The stirrer rotates in the slurry to cause a flow of slurry in a circumferential direction.

It is also possible to use an independent dipping tank for separately dipping each solid electrolytic body into a slurry stored in this independent dipping tank. Namely, the number of independent dipping tanks is equal to the number of solid electrolytic bodies to be dipped simultaneously. By lowering the jig hanging the plurality of solid electrolytic bodies into respective dipping tanks, each solid electrolytic body is dipped into the slurry stored in the corresponding dipping tank.

Each solid electrolytic body is rotatable about its own axis when hung down from the jig. When the solid electrolytic body is dipped into the slurry, the solid electrolytic body rotates in the slurry. It is however possible to stop the rotation of the solid electrolytic body when the solid electrolytic body is dipped into the slurry.

It is possible to remove the stirrer when the solid electrolytic body rotates about its own axis when hung down from the jig.

However, according to the conventional dipping method for the solid electrolytic body, the slurry concentration and the slurry component in the dipping tank tends to be nonuniform when a slurry having high viscosity is used. The condition of the slurry film coated on the outside electrode becomes different in each solid electrolytic body.

In other words, performance and characteristics of the porous layer is not constant according to the conventional dipping method. The manufactured gas sensors will have performances different from each other.

SUMMARY OF THE INVENTION

In view of the problems of the conventional dipping method, the present invention has an object to provide a method for manufacturing a gas sensing element having a uniform porous layer.

In order to accomplish the above and other related objects, the present invention provides a first method for manufacturing a gas sensing element which has a cup-shaped solid electrolytic body having a reference gas chamber formed therein, an inside electrode provided on an inner surface of the solid electrolytic body, an outside electrode provided on an outer surface of the solid electrolytic body, and a porous layer formed so as to cover the outside electrode. The first manufacturing method comprises a step of forming the solid electrolytic body, a step of providing the inside electrode on a predetermined portion of the inner surface of the solid electrolytic body and providing the outside electrode on a predetermined portion of the outer surface of the solid electrolytic body, and a step of dipping the solid electrolytic body into a slurry which is prepared for forming the porous layer by using a dipping apparatus.

The dipping apparatus used in the first manufacturing method comprises a dipping tank for storing the slurry which is prepared for forming the porous layer, a viscosity adjusting tank equipped with a viscosity sensor for measuring a viscosity of the slurry and a viscosity adjusting mechanism for adjusting the viscosity of the slurry based on a sensing value of the viscosity sensor, a fluid passage for connecting the dipping tank and the viscosity adjusting tank, and a circulating pump provided in the fluid passage for forcibly circulating the slurry between the dipping tank and the viscosity adjusting tank.

The dipping step of the first manufacturing method includes a step of dipping the solid electrolytic body into the slurry stored in the dipping tank while the slurry is forcibly circulated between the dipping tank and the viscosity adjusting tank by the circulating pump, a step of forming a slurry film on a predetermined portion of the solid electrolytic body through this dipping treatment, and a step of sintering the slurry film to form the porous layer.

The dipping apparatus of the first manufacturing method comprises the viscosity adjusting tank. The slurry is forcibly circulated between the viscosity adjusting tank and the dipping tank. Thus, the slurry is always stirred. The concentration and viscosity of the slurry used for dipping solid electrolytic bodies can be always kept to a uniform and constant value.

It becomes possible to accurately equalize the condition of a slurry film coated on each solid electrolytic body. Hence, performance and characteristics of the porous layer are constant in each solid electrolytic body. The manufactured gas sensors show the same performances.

The porous layer of the gas sensing element of this invention functions as trap layer.

The outside electrode needs to be exposed to a measured gas atmosphere during detection of gas concentration. When the measured gas contains poisonous or harmful substances, the trap layer is provided to protect (i.e., cover) the outside electrode and the gas sensing element. The trap layer traps the poisonous or harmful substances and assures accurate detection of gas concentration.

Furthermore, it is possible to provide an additional layer on the porous layer. Furthermore, it is possible to provide a second trap layer on the porous layer.

Furthermore, when the outside electrode is provided on the solid electrolytic body and the additional layer is provided on the outside electrode, it is preferable to provide the porous layer so as to cover the additional layer according to the manufacturing method of the present invention. The additional layer is, for example, a protective layer or the like as shown in the later-described embodiments.

In general, the porous layer of the present invention is provided to cover the entire surface of the outside electrode. However, it is possible to provide the porous layer so as to partly cover the outside electrode.

Furthermore, it is possible to provide the porous layer so as to cover other portion of the solid electrolytic solid electrolytic body other than the outside electrode.

Furthermore, the dipping apparatus used in the first manufacturing method is equipped with the viscosity adjusting tank. The viscosity adjusting tank has a function of maintaining the viscosity (i.e., concentration) of slurry stored in the dipping tank at a constant value. Accordingly, it becomes possible to prepare uniform slurry preferable for the dipping treatment.

The viscosity adjustment of slurry is performed by the viscosity adjusting mechanism. The viscosity adjusting mechanism is responsive to a sensing value of the viscosity sensor. When the viscosity of slurry deviates from a predetermined value, the viscosity adjusting mechanism adds an appropriate amount of water into the viscosity adjusting tank based on a sensing value of the viscosity sensor.

Furthermore, the slurry is always and forcibly circulated. This is effective to prevent the surficial slurry film from appearing on the surface of the slurry. It is also effective to prevent the slurry from sedimenting on the bottom of the dipping tank.

According to the first manufacturing method of the present invention, it is preferable that the dipping tank has a fluid inlet port for introducing the slurry from the viscosity adjusting tank, a receiving groove is provided along an opening of the dipping tank so as to surround a circumferential upper end of the dipping tank to receive the slurry overflowed from the dipping tank, and a fluid outlet port provided in the receiving groove for discharging the overflowed slurry to the viscosity adjusting tank.

With this arrangement, it becomes possible to circulate the slurry in a wide region ranging from the bottom to the upper opening of the dipping tank. Especially, it becomes possible to promote the flow of slurry in the vicinity of the surface of slurry stored in the dipping tank.

According to the first manufacturing method of the present invention, it is preferable that a baffle is provided in the dipping tank so as to be positioned adjacent to the fluid inlet port so that flow of the slurry introduced from the viscosity adjusting tank collides with the baffle.

Figure 4:
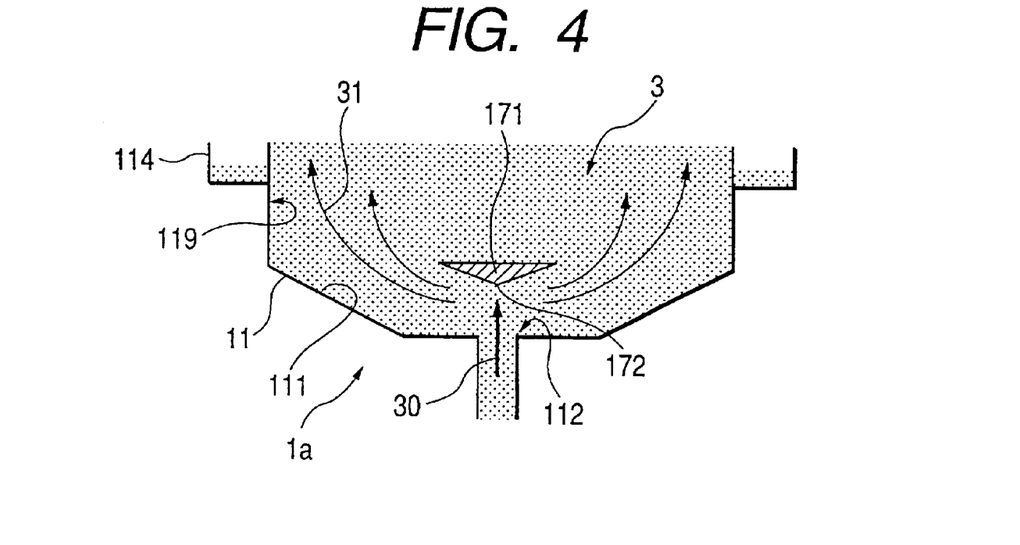
FIG. 4 is a schematic view showing a dipping tank equipped with a baffle in accordance with a second embodiment of the present invention.

According to this arrangement, the slurry flowing into the dipping tank from the fluid inlet port is guided by the baffle so as to diffuse in all radial directions (refer to FIG. 4). The flowing speed of the slurry increases. The slurry is smoothly circulated upward from the bottom of the dipping tank. It becomes possible to eliminate the sediment of slurry.

A predetermined gap is provided between the baffle and the fluid inlet port so that the introduced slurry smoothly flows.

According to the first manufacturing method of the present invention, it is preferable that a porous stirring plate is provided in the dipping tank, and the stirring plate oscillate in the dipping tank.

With this arrangement, it becomes possible to surely stir the slurry stored in the dipping tank. It becomes possible to eliminate the sediment of slurry. Furthermore, it becomes possible to provide the slurry having constant and uniform concentration and viscosity.

Figure 6:
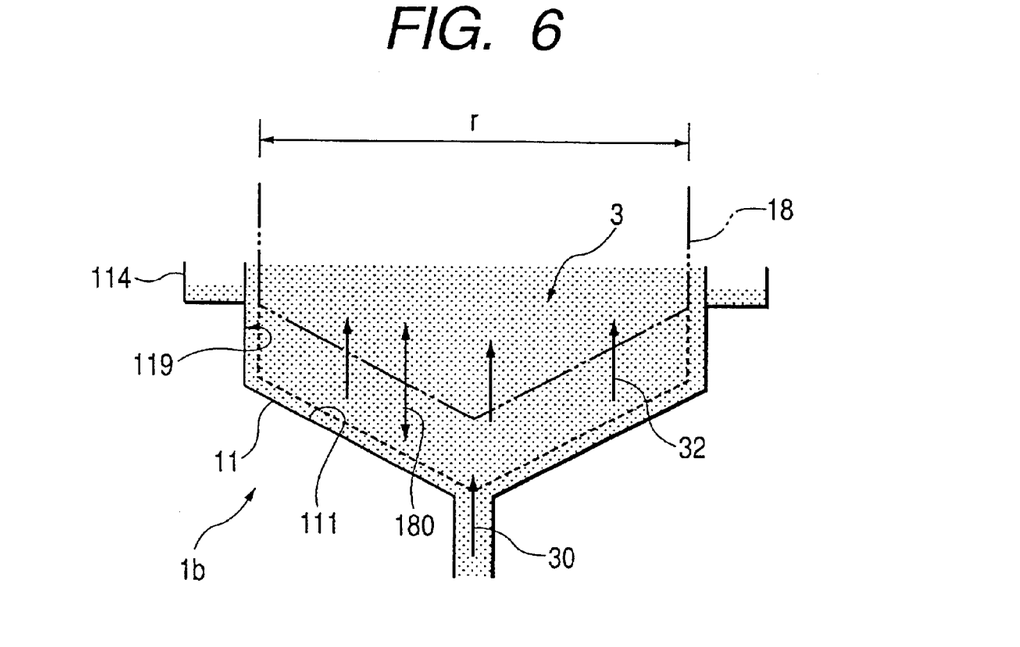
FIG. 6 is a schematic view showing a dipping tank equipped with a stirring plate in accordance with a third embodiment of the present invention.

Furthermore, it is preferable that the stirring plate has a configuration just fitting to the inner wall of the dipping tank (refer to FIG. 6). This realizes easy stirring of slurry stored in the dipping tank.

Furthermore, the present invention provides a second method for manufacturing a gas sensing element which has a cup-shaped solid electrolytic body having a reference gas chamber formed therein, an inside electrode provided on an inner surface of the solid electrolytic body, an outside electrode provided on an outer surface of the solid electrolytic body, and a porous layer formed so as to cover the outside electrode. The second manufacturing method comprises a step of forming the solid electrolytic body, a step of providing the inside electrode on a predetermined portion of the inner surface of the solid electrolytic body and providing the outside electrode on a predetermined portion of the outer surface of the solid electrolytic body, and a step of dipping the solid electrolytic body into a slurry which is prepared for forming the porous layer by using a dipping apparatus.

The dipping apparatus used in the second manufacturing method comprises a dipping tank for storing the slurry which is prepared for forming the porous layer, a first stirrer shiftable in a circumferential direction along an opening of the dipping tank to stir the slurry, and a second stirrer rotatable in the vicinity of a bottom of the dipping tank to stir the slurry.

The dipping step of the second manufacturing method includes a step of dipping the solid electrolytic body into the slurry stored in the dipping tank, a step of forming a slurry film on a predetermined portion of the solid electrolytic body through this dipping treatment, and a step of sintering the slurry film to form the porous layer.

According to the second manufacturing method, the slurry is stirred by the first stirrer shiftable in the circumferential direction along the opening of the dipping tank. Furthermore, the slurry is stirred by the second stirrer rotatable in the vicinity of the bottom of the dipping tank. Hence, the first stirrer and the second stirrer are effectively used to stir the slurry from the bottom to the vicinity of the opening of the dipping tank. Thus, it becomes possible to entirely stir the slurry stored in the dipping tank.

The concentration and viscosity of the slurry used for dipping solid electrolytic bodies can be always kept to a uniform and constant value.

It becomes possible to accurately equalize the condition of a slurry film coated on each solid electrolytic body. Hence, performance and characteristics of the porous layer are constant in each solid electrolytic body. The manufactured gas sensors show the same performances.

The dipping apparatus used in the second manufacturing method is a single tank type which is simple in arrangement. This is effective to manufacture the gas sensing element at low cost.

Furthermore, the slurry can be effectively stirred in the vicinity of the bottom of the dipping tank as well as in the vicinity of the upper opening of the dipping tank. This is effective to prevent the surficial slurry film from appearing on the surface of the slurry. It is also effective to prevent the slurry from sedimenting on the bottom of the dipping tank.

According to the second manufacturing method of the present invention, it is preferable that the first stirrer is a stirring rod provided in the vicinity of the opening of the dipping tank so as to be shiftable in the circumferential direction along an inner wall surface of the dipping tank, and the second stirrer is rotary vanes rotatable about a rotary shaft provided on the bottom of the dipping tank.

With this arrangement, it becomes possible to simultaneously stir the slurry in the vicinity of the bottom of the dipping tank as well as in the vicinity of the upper opening of the dipping tank. Accordingly, it becomes possible to thoroughly stir the slurry stored in the dipping tank. Furthermore, it becomes possible to prevent the surficial slurry film from appearing on the surface of the slurry. Thus, this arrangement is preferable for the slurry having higher viscosity or applicable to the dipping treatment using a large-size dipping tank. When a large-size dipping tank is used, numerous solid electrolytic bodies can be dipped at a time. This improves the productivity.

According to the first or second manufacturing method of the present invention, it is preferable that a ceramic protective layer is formed on the solid electrolytic body before the solid electrolytic body is dipped into the slurry.

According to the first or second manufacturing method of the present invention, it is preferable that the solid electrolytic body is rotated when the solid electrolytic body is dipped into the slurry. This is effective to form a uniform slurry film on each solid electrolytic body.

According to the first or second manufacturing method of the present invention, it is preferable that the solid electrolytic body is stationary when the solid electrolytic body is dipped into the slurry. This arrangement is appropriate to use a large-size dipping tank which is capable of dipping many solid electrolytic bodies at a time. The efficiency of dipping treatment can be improved.

In any of the first and second manufacturing method of the present invention, it is possible to form a uniform and same porous layer on each solid electrolytic body.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

Preferred embodiments of the present invention will be explained hereinafter with reference to attached drawings. Identical parts are denoted by the same reference numerals throughout the drawings.

First Embodiment

Hereinafter, a gas sensing element manufacturing method according to a preferred embodiment of the present invention will be explained.

Figure 2:
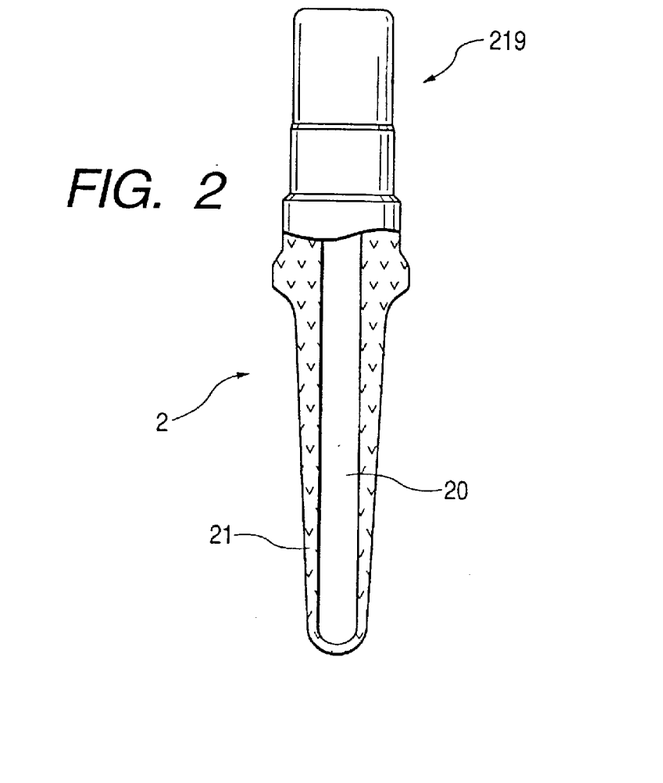
FIG. 2 is a partly cross-sectional view showing a solid electrolytic body of a gas sensing element in accordance with the first embodiment of the present invention.
Figure 3:
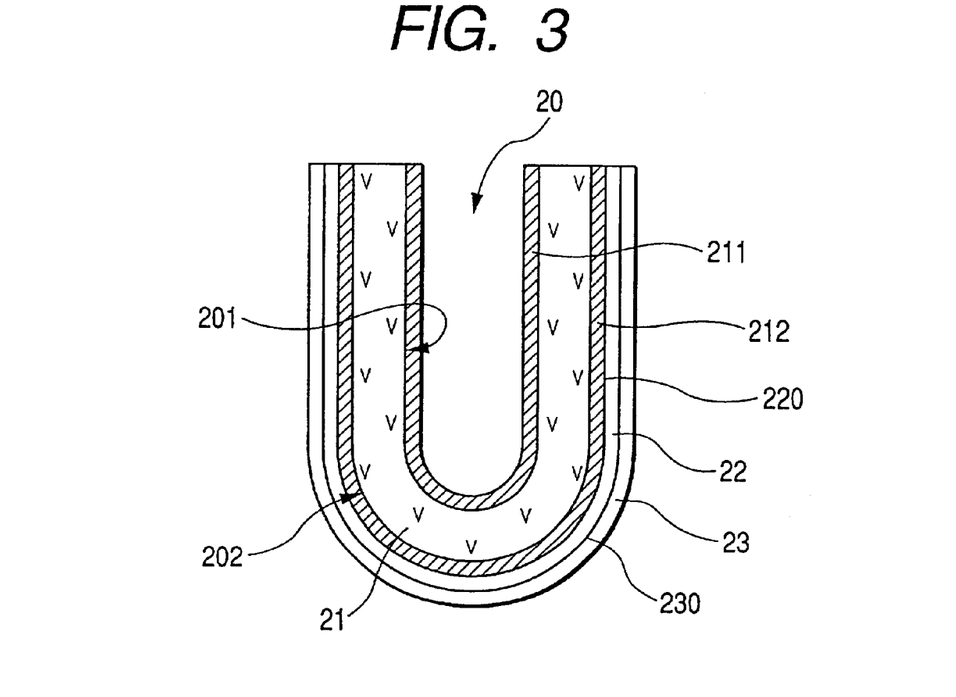
FIG. 3 is a vertical cross-sectional view showing a detailed arrangement of the gas sensing element in accordance with the first embodiment of the present invention.

FIGS. 2 and 3 show a gas sensing element 2 of a gas sensor in accordance with a first embodiment of the present invention. The gas sensing element 2 has a cup-shaped solid electrolytic body 21 with a reference gas chamber 20 defined therein. An inside electrode 211 is provided on an inner surface 201 of solid electrolytic body 21. An outside electrode 212 is provided on an outer surface 202 of solid electrolytic body 21. A porous layer 23 covers the outside electrode 212.

The gas sensing element 2 is manufactured in the following manner.

First, the solid electrolytic body 21 is manufactured. Then, the inside electrode 211 and the outside electrode 212 are provided at predetermined portions of the inner surface 201 and the outer surface 202 of the solid electrolytic body 21, respectively. Then, the solid electrolytic body 21 is dipped into a slurry 3. The slurry 3 is prepared for forming the porous layer 23.

Figure 1:
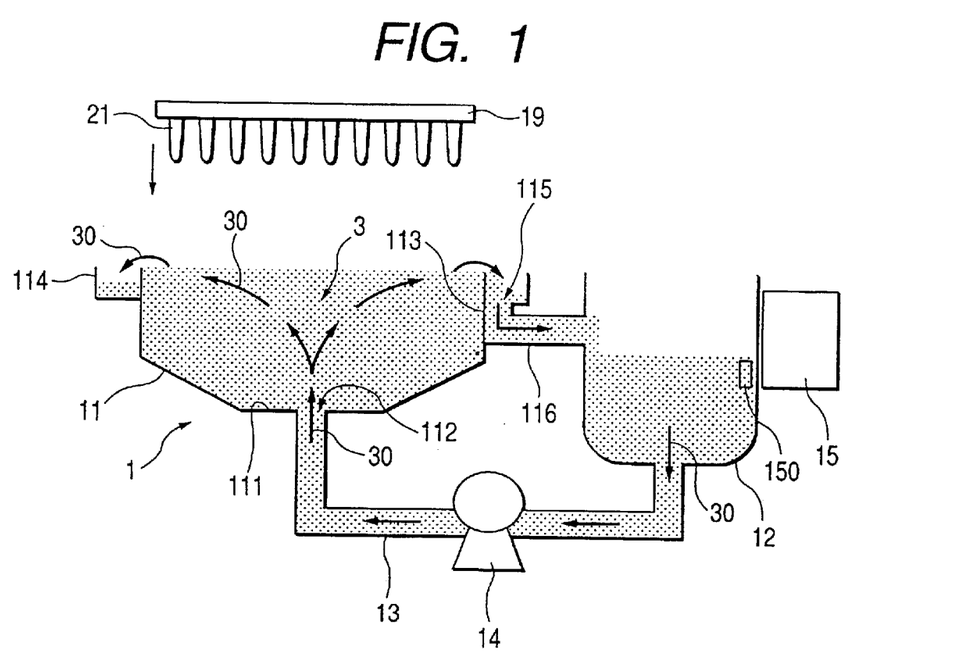
FIG. 1 is a schematic view showing the arrangement of a dipping apparatus in accordance with a first embodiment of the present invention.

FIG. 1 shows the arrangement of a dipping apparatus 1 in accordance with this embodiment. The solid electrolytic body 21 is dipped into the slurry 3 stored in the dipping tank 11. The dipping tank 11 is connected to a viscosity adjusting tank 12 via an overflow passage 116. The slurry 3 is thus conveyed into the viscosity adjusting tank 12. A viscosity sensor 150 is provided in the viscosity adjusting tank 12. A viscosity adjusting mechanism 15 is associated with the viscosity sensor 150. The viscosity adjusting mechanism 15 adjusts the viscosity of slurry 3 based on a sensing value of the viscosity sensor 150. The viscosity adjusted slurry is returned to the dipping tank 11 via a circulation passage 13. A circulating pump 14 is provided in the circulation passage 13. The circulating pump 14 forcibly feeds the viscosity adjusted slurry from the viscosity adjusting tank 12 to the dipping tank 11.

While the slurry 3 is forcibly circulated between the dipping tank 11 and the viscosity adjusting tank 12 by the circulating pump 14, the solid electrolytic body 21 is dipped into the slurry 3 stored in the dipping tank 11.

Through the dipping treatment, a slurry film is coated on a predetermined portion of the solid electrolytic body 21. Then, the slurry film is sintered to form the porous layer 23.

Hereinafter, the manufacturing method of the gas sensing element in accordance with this embodiment will be explained in more detail.

The gas sensing element 2 of this embodiment is attached to an exhaust gas passage of an automotive engine. The gas sensing element 2 is employed to detect the oxygen concentration in the exhaust gas to control an air-fuel ratio of an automotive engine. In other words, the gas sensing element 2 functions as part of the fuel combustion control system or the exhaust gas purification system.

The gas sensing element 2, as shown in FIGS. 2 and 3, comprises the cup-shaped solid electrolytic body 21 made of an oxygen ion conductive zirconia, the inside electrode 211 provided on the inner surface 201 of solid electrolytic body 21, and the outside electrode 212 provided on the outer surface 202 of solid electrolytic body 21. The inside electrode 211 provided on the inner surface 201 of solid electrolytic body 21 is exposed to a reference gas (e.g., air) filled in the reference gas chamber 20 defined in the solid electrolytic body 21. The outside electrode 212 provided on the outer surface 202 of solid electrolytic body 21 is exposed to the exhaust gas of the automotive engine.

Although not shown in the drawing, to detect an output of the gas sensing element 2, leads and terminals of the inside electrode 211 and the outside electrode 212 of gas sensing element 2 are provided on the inner and outer surfaces 201 and 202 of solid electrolytic body 21.

The inside electrode 211 and the outside electrode 212 are platinum electrodes.

An alumina ceramic protective layer 22 is provided on a surface 220 of outside electrode 212. The protective layer 22 is formed by plasma spray coating. The protective layer 22 has slight gas permeability. The porous layer 23 covers a surface 230 of the protective layer 22. The porous layer 23 functionally serves as a trap layer for trapping poisonous or harmful substances contained in the exhaust gas (i.e., the objective gas to be measured). The protective layer 22 functionally serves as a diffusion resistive layer which controls the time required for the exhaust gas to reach the outside electrode 212. The protective layer 22 (i.e., the diffusion resistive layer) also controls the amount of the exhaust gas reaching the outside electrode 212.

Next, the method for manufacturing the gas sensing element 2 of this invention will be explained.

First, the powdery raw material of solid electrolytic body 21 is prepared. The powdery raw material of solid electrolytic body 21 comprises zirconia and yttria. The inside electrode 211 and the outside electrode 212 are formed on the predetermined portions of the solid electrolytic body 21 by chemical plating (refer to FIGS. 2 and 3). The alumina ceramic protective layer 22 is provided on the surface 220 of outside electrode 212 by plasma spray coating. Next, the porous layer 23 serving as trap layer is provided on the surface 230 of protective layer 22.

Next, the dipping apparatus 1 used for forming the porous layer 23 is explained.

As shown in FIG. 1, the dipping apparatus 1 comprises the dipping tank 11 filled with the slurry 3 into which the solid electrolytic body 21 is dipped. The dipping tank 11 is connected to the viscosity adjusting tank 12 via the overflow passage 116. The slurry 3 flows into the viscosity adjusting tank 12 via the overflow passage 116. The viscosity sensor 150, detecting the viscosity of slurry 3, is provided in the viscosity adjusting tank 12. The viscosity adjusting mechanism 15, associated with the viscosity sensor 150, adjusts the viscosity of slurry 3 based on a sensing value of the viscosity sensor 150. The bottom of viscosity adjusting tank 12 is connected to the bottom of dipping tank 11 via the circulation passage 13. The circulating pump 14 is provided in the circulation passage 13 to forcibly return the viscosity adjusted slurry from the viscosity adjusting tank 12 to the dipping tank 11.

The dipping tank 11 has an opening 113. A receiving groove 114 is provided along the upper end (i.e., along the opening 113) of an outer surface of dipping tank 11. In other words, the receiving groove 114 surrounds the circumferential upper end of the dipping tank 11. The slurry 3, when overflowed from the dipping tank 11, is received by the receiving groove 114.

A fluid inlet port 112 is formed at a bottom 111 of dipping tank 11. The viscosity adjusted slurry 3 is supplied from the viscosity adjusting tank 12 via the circulation passage 13 into the dipping tank 11 from the fluid inlet port 112. A fluid outlet port 115 is formed in the receiving groove 114. The overflowed slurry 3 flows into the viscosity adjusting tank 12 via the overflow passage 116.

The above-described dipping apparatus 1 is used to form a slurry film on the outside electrode 212 of solid electrolytic body 21. As shown in FIG. 1, a jig 19 is prepared to hang a plurality of solid electrolytic bodies 21. The jig 19 is a pallet having a plurality of holding recesses formed at its lower surface for fixing the solid electrolytic bodies 21. As shown in FIG. 2, the solid electrolytic body 21 has a proximal portion 219. The proximal portion 219 of solid electrolytic body 21 is inserted into the holding recess of the jig 19. Each solid electrolytic body 21 is securely fixed to the jig 19 by press fitting or any other fixing means or method.

The total number of solid electrolytic bodies 21 attachable to the jig 19 can be increased to 100 when the sizes of jig 19 and dipping tank 11 are large. In other words, according to the dipping apparatus 1 shown in FIG. 1, 100 or more solid electrolytic bodies 21 can be simultaneously dipped into the slurry 3.

The dipping treatment of this embodiment is performed in the following manner.

The slurry 3 stored in a pot is stirred with a pot mill to prepare the slurry 3 having uniform concentration. Then, water is added to the slurry 3 to adjust the viscosity of slurry 3. The thus formed slurry 3 has a very high viscosity of 450 mPa·s.

The slurry 3 is supplied or introduced into the dipping tank 11 and the viscosity adjusting tank 12. Next, the circulating pump 14 is driven to circulate the slurry 3 between the dipping tank 11 and the viscosity adjusting tank 12 as shown by arrow 30 in FIG. 1.

The slurry 3 enters into the dipping tank 11 from the fluid inlet port 112 and forms the fluid stream directed upward from the bottom 111 of dipping tank 11 to the liquid surface of the slurry 3. A part of slurry 3 overflows into the receiving groove 114. The slurry 3 stored in the receiving groove 114 flows into the viscosity adjusting tank 12 via the fluid outlet port 115.

Under the condition where the slurry 3 circulates in the dipping tank 11, the jig 19 hanging the plurality of solid electrolytic bodies 21 is positioned just above the opening 113 of the dipping tank 11 as shown in FIG. 1. The jig 19 is lowered to dip the plurality of solid electrolytic bodies 21 into the slurry 3 stored in the dipping tank 11.

After a predetermined time has passed, the jig 19 is raised upward to take the plurality of solid electrolytic bodies 21 out of the slurry 3 stored in the dipping tank 11. Then, the plurality of solid electrolytic bodies 21 hung on the jig 19 are conveyed into a drier to dry and heat them. Through the drying and heating treatment, a slurry film is formed on a predetermined portion of each solid electrolytic body 21.

Subsequently, respective solid electrolytic bodies 21 are removed from the jig 19. Each solid electrolytic body 21 is then sintered to change the slurry film into the porous layer 23. Thus, the gas sensing element 2 of this embodiment is obtained.

Before the next set of a plurality of solid electrolytic bodies 21 is dipped into the slurry 3, the viscosity sensor 150 measures the viscosity of slurry 3 stored in the viscosity adjusting tank 12. Namely, the viscosity sensor 150 detects the viscosity of the slurry 3 returned from the dipping tank 11. When the measured viscosity value of slurry 3 is higher than a predetermined value, the viscosity adjusting mechanism 15 adds an appropriate amount of water into the viscosity adjusting tank 12 to reduce the slurry concentration.

With this adjustment, it becomes possible to dip the plurality of solid electrolytic bodies 21 into the slurry 3 whose concentration is always constant or stable.

The dipping treatment of this embodiment has the following function and effects.

The dipping apparatus 1 of this embodiment comprises the viscosity adjusting tank 12. The slurry 3 is forcibly circulated between the viscosity adjusting tank 12 and the dipping tank 11. Thus, the slurry 3 is always stirred. The concentration and viscosity of the slurry 3 used for dipping solid electrolytic body 21 can be always kept to a uniform and constant value.

As the dipping tank 11 is widely opened to the air as shown in FIG. 1, the concentration of slurry 3 tends to become large with elapsing time. According to this embodiment, the viscosity sensor 150 always monitors the viscosity of slurry 3 stored in the viscosity adjusting tank 12. The viscosity adjusting mechanism 15, associated with the viscosity sensor 150, adds an appropriate amount of water to the slurry 3 to adjust the viscosity of slurry 3 to a desired value.

Accordingly, the first embodiment of the present invention realizes the dipping treatment for the solid electrolytic body 21 under the condition that the slurry 3 is always kept to a uniform and constant value.

According to the above-described embodiment, each solid electrolytic body is held in a stationary condition with respect to the dipping tank. However, it is also possible to rotate each solid electrolytic body during the dipping treatment.

Second Embodiment

The second embodiment provides a dipping apparatus 1a to form a slurry film on an outside electrode of a solid electrolytic body. The dipping apparatus 1a of the second embodiment is similar to the dipping apparatus 1 shown in FIG. 1 except for a baffle 171.

As shown in FIG. 4, the baffle 171 is provided in the dipping tank 11 of the dipping apparatus 1a.

The baffle 171 has a flattened conical body supported reversely and extending horizontally. An apical end (i.e., pinnacle) 172 of baffle 171 is directed toward the fluid inlet port 112 opened on the bottom 111 of dipping tank 11.

According to the arrangement of the second embodiment, the slurry 3 is forcibly introduced into the dipping tank 11 from the fluid inlet port 112 as shown by arrow 30. The flow of slurry 3 collides with the apical end 172 of baffle 171. Then, the slurry 3 flows upward along the reversed conical surface of the baffle 171 as well as along an inner wall surface 119 of dipping tank 11 as shown by arrow 31. The velocity of flowing slurry 3 is increased in this moment.

The rest of the arrangement of second embodiment is substantially the same as that of the first embodiment.

Figure 5:
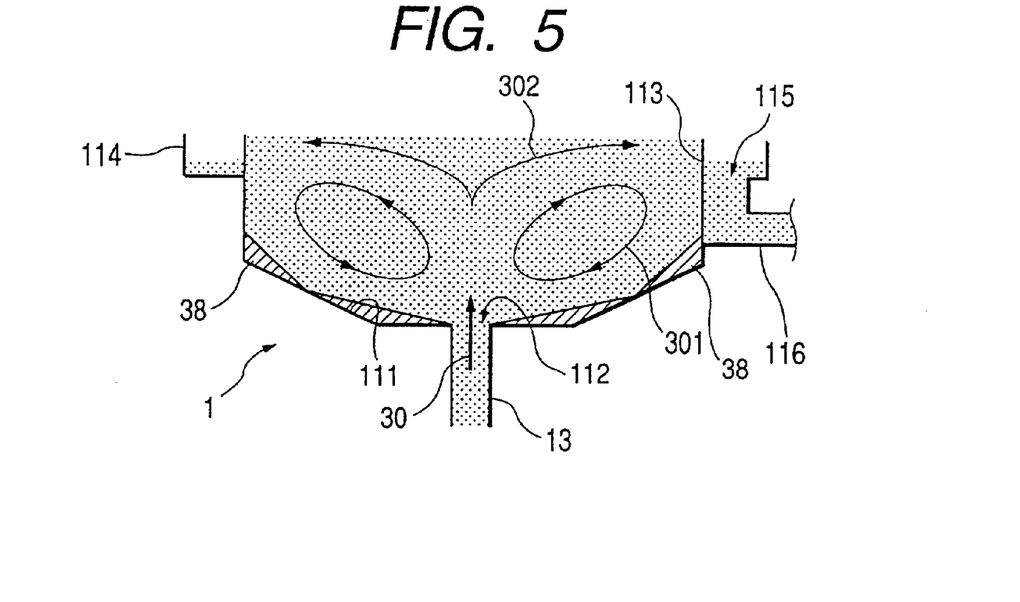
FIG. 5 is a schematic view showing slurry sediment on a bottom of a dipping tank in accordance with the second embodiment of the present invention.

Providing the baffle 171 in the vicinity of the fluid inlet port 112 of dipping tank 11 is effective to eliminate the convection of slurry 3. FIG. 5 shows the convection of slurry 3 (refer to arrow 301).

Once the convection of slurry 3 is caused in the dipping tank 11, the newly introduced slurry 3 (indicated by allow 30 in FIG. 5) immediately reaches the liquid surface of slurry 3 stored in the dipping tank 11 (refer to arrow 302).

Under the condition that the convection of slurry 3 is formed in the dipping tank 11, there is the possibility that sediment 38 of slurry 3 appears on the bottom 111 of dipping tank 11 (refer to FIG. 5). Especially, when the velocity of flowing slurry 3 is slow or when the viscosity of slurry 3 is high, there is the tendency that a relatively large amount of slurry 3 sediments.

In this respect, the baffle 171 of the second embodiment effectively prevents the high-viscous slurry 3 from settling on the bottom 111 of dipping tank 11. Thus, the second embodiment provides the dipping apparatus 1a which is capable of effectively eliminating the slurry sediment 38.

Third Embodiment

The third embodiment provides a dipping apparatus 1b to form a slurry film on an outside electrode of a solid electrolytic body. The dipping apparatus 1b of the third embodiment is similar to the dipping apparatus 1 shown in FIG. 1 except for a stirring plate 18.

As shown in FIG. 6, the stirring plate 18 is provided in the dipping tank 11 of dipping apparatus 1b. The stirring plate 18 is made of a porous member. The slurry 3 is permeable through the stirring plate 18. The stirring plate 18 is shiftable in the up-and-down direction in the dipping tank 11 as shown by arrow 180 in FIG. 6.

The stirring plate 18 has a configuration just fitted to the bottom 111 and the inner wall surface 119 of dipping tank 11. More specifically, the stirring plate 18 is a cup-shaped wire mesh having the configuration similar to the dipping tank 11. The mesh size (i.e., aperture) of stirring plate 18 is 3 mm. The cup diameter 'r' is 325 mm.

The dipping apparatus 1b of this embodiment is used in the following manner.

First, the slurry 3 is supplied or introduced into the dipping tank 11 and the viscosity adjusting tank of the dipping apparatus 1b. The viscosity adjusting tank of the third embodiment is substantially identical with that of the first embodiment.

Then, the circulating pump is driven to forcibly circulate the slurry 3 between the dipping tank 11 and the viscosity adjusting tank. The stirring plate 18 is set in the dipping tank 11 beforehand.

In this condition, the stirring plate 18 is repetitively oscillated in the up-and-down direction as shown by arrow 180. The repetitive up-and-down movement of stirring plate 18 forms the fluid stream directed upward from the bottom 111 of dipping tank 11 to the liquid surface of the slurry 3 (refer to arrow 32). The thus generated fluid stream effectively stirs the slurry 3 from the bottom 111 and, as a result, provides the slurry 3 having a uniform concentration.

Thereafter, the jig 19 (refer to the first embodiment) hanging a plurality of solid electrolytic bodies 21 is positioned just above the dipping tank 11. The jig 19 is lowered toward the dipping tank 11 to dip the plurality of solid electrolytic bodies 21 into the slurry 3 stored in the dipping tank 11.

After a predetermined time has passed, the jig 19 is raised upward to take the plurality of solid electrolytic bodies 21 out of the slurry 3 stored in the dipping tank 11. Then, the plurality of solid electrolytic bodies 21 hung on the jig 19 are conveyed into a drier to dry and heat them. Through the drying and heating treatment, a slurry film is formed on a predetermined portion of each solid electrolytic body 21.

Subsequently, respective solid electrolytic bodies 21 are removed from the jig 19. Each solid electrolytic body 21 is then sintered to change the slurry film into the porous layer 23. Thus, the gas sensing element 2 of this embodiment is obtained.

The rest of the arrangement of third embodiment is substantially the same as that of the first embodiment.

According to the third embodiment, the stirring plate 18 is effectively used to stir the slurry 3 from the bottom 111 of dipping tank 11. It becomes possible to prevent the slurry 3 from sedimenting. It becomes possible to provide uniform slurry 3 having the constant concentration and viscosity.

Furthermore, it is needless to say that removal of slurry sediment is not required.

Fourth Embodiment

Figure 7:
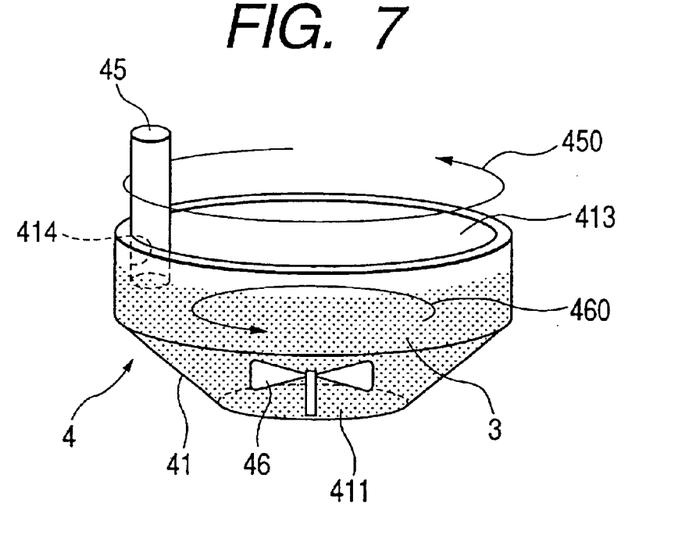
FIG. 7 is a perspective view explaining the operation of first and second stirrers in accordance with a fourth embodiment of the present invention.

FIG. 7 shows a dipping apparatus 4 used for forming a slurry film on an outside electrode of a solid electrolytic body in accordance with the fourth embodiment.

The dipping apparatus 4 according to the fourth embodiment consists of a dipping tank 41, a first stirrer 45, and a second stirrer 46.

The first stirrer 45 is a stirring rod provided in the vicinity of an opening 413 of dipping tank 41. The first stirrer 45 is shiftable in a circumferential direction of the opening 413 along an inner wall surface 414 of dipping tank 41 (refer to arrow 450 shown in FIG. 7).

The second stirrer 46 is rotary vanes rotatable about a rotary shaft provided on a bottom 411 of dipping tank 41 (refer to arrow 460). The rotary shaft of second stirrer 46 is coaxial with the central axis of dipping tank 41.

Although not shown in the drawing, the first stirrer (i.e., stirring rod) 45 and the second stirrer (i.e., rotary vanes) 46 are driven by a motor.

The dipping apparatus 4 of the fourth embodiment is used to form a slurry film on an outside electrode of a solid electrolytic body.

The slurry 3 is supplied or introduced into the dipping tank 41 of dipping apparatus 4. Next, the first stirrer 45 and the second stirrer 46 are driven to stir the slurry 3 sufficiently. After a predetermined time has passed, the first stirrer 45 and the second stirrer 46 are stopped.

Thereafter, the jig 19 (refer to the first embodiment) hanging a plurality of solid electrolytic bodies 21 is positioned just above the opening 413 of dipping tank 41. The jig 19 is lowered to dip the plurality of solid electrolytic bodies 21 into the slurry 3 stored in the dipping tank 41.

After a predetermined time has passed, the jig 19 is raised upward to take the plurality of solid electrolytic bodies 21 out of the slurry 3 stored in the dipping tank 41. Then, the plurality of solid electrolytic bodies 21 hung on the jig 19 are conveyed into a drier to dry and heat them. Through the drying and heating treatment, a slurry film is formed on a predetermined portion of each solid electrolytic body 21.

Subsequently, respective solid electrolytic bodies 21 are removed from the jig 19. Each solid electrolytic body 21 is then sintered to change the slurry film into the porous layer 23. Thus, the gas sensing element 2 of this embodiment is obtained.

The rest of the arrangement of fourth embodiment is substantially the same as that of the first embodiment.

According to the fourth embodiment, the first stirrer 45 and the second stirrer 46 are effectively used to stir the slurry 3 from the bottom 111 of dipping tank 11 to the vicinity of opening 413. Thus, it becomes possible to entirely stir the slurry 3 stored in the dipping tank 41.

Figure 8:
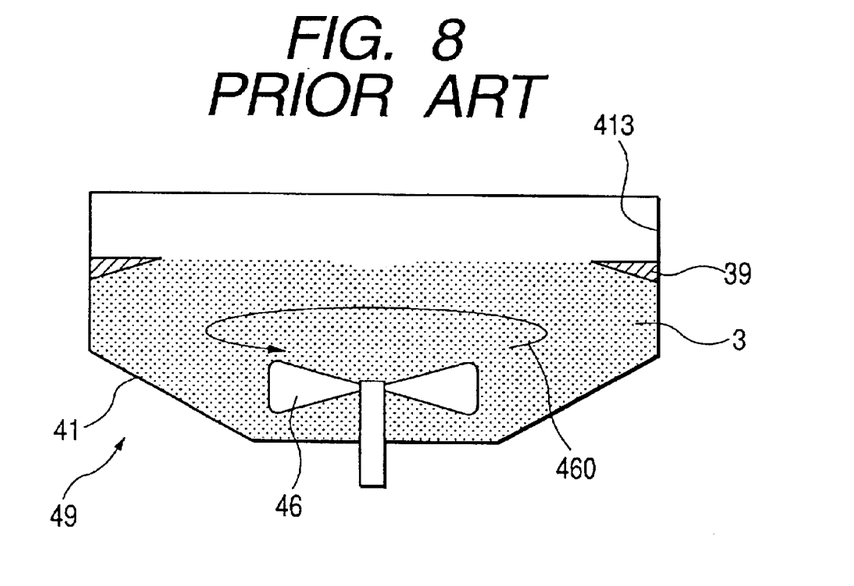
FIG. 8 is a schematic view showing a conventional dipping tank equipped with stirring vanes provided on its bottom.

FIG. 8 shows a conventional dipping apparatus 49 which is not equipped with the first stirrer 45. According to this conventional dipping apparatus 49, the slurry 3 staying in the vicinity of a bottom 41 of dipping tank 41 is stirred by the second stirrer 46 as shown by arrow 460.

However, when the viscosity of slurry 3 is high, there is the possibility that a slurry surficial film 39 is formed along the opening 413 of slurry tank 41. This causes dispersion in the coating weight of slurry 3 to be applied on the solid electrolytic body 21. Especially, when numerous solid electrolytic bodies 21 are dipped into the slurry 3 at a time, coating weight of slurry 3 tends to vary depending on the position of each solid electrolytic body 21 with respect to the jig (i.e., pallet) 19.

The dipping apparatus 4 of the fourth embodiment makes it possible to eliminate the slurry surficial film 39 appearing on the liquid surface of slurry 3. It becomes possible to equalize the coating weight of slurry 3 applied to each solid electrolytic body 21.

Furthermore, it is needless to say that removal of slurry sediment is not required.

Fifth Embodiment

The fifth embodiment is characterized in that each solid electrolytic body 21 is dipped into an independent or separate dipping tank 11.

Figure 9:
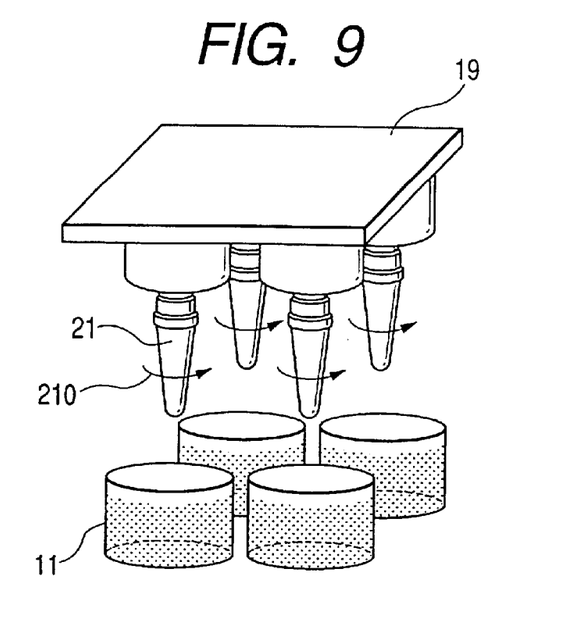
FIG. 9 is a perspective view showing separate slurry tanks each provided for dipping a single solid electrolytic body in accordance with a fifth embodiment of the present invention.

FIG. 9 shows the independent or separate dipping tanks 11 each storing slurry 3 for dipping only one solid electrolytic body 21. The number of dipping tanks 11 is equal to the number of solid electrolytic bodies 21 to be dipped simultaneously. The jig 19 hangs the solid electrolytic bodies 21 to be dipped simultaneously. Although not shown in the drawing, the jig 19 is equipped with a rotating mechanism for rotating each solid electrolytic body 21 about its central axis (refer to arrow 210).

When the solid electrolytic body 21 is dipped into the slurry 3 stored in dipping tank 11, the solid electrolytic body 21 rotates in the slurry 3.

Each dipping tank 11 of FIG. 9 is the one disclosed in any one of the first to fourth embodiments of the present invention.

The rest of the arrangement is substantially the same as that of the first embodiment.

Figure 10:
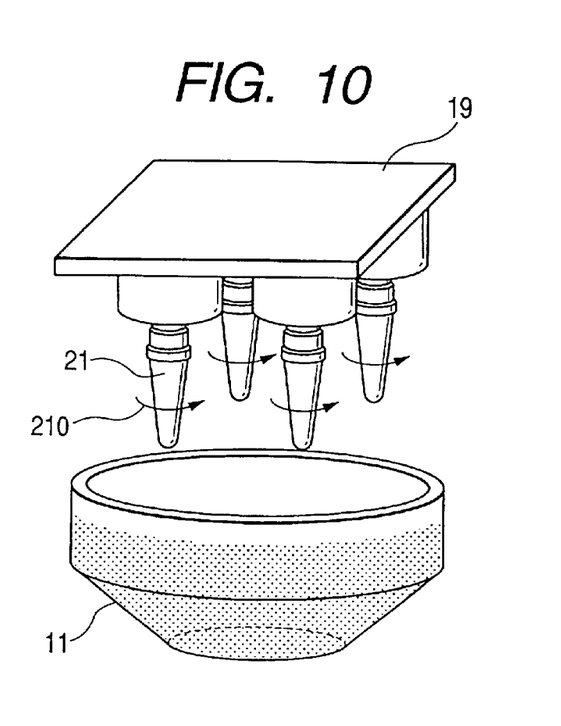
FIG. 10 is a perspective view showing a common dipping tank for dipping a plurality of solid electrolytic bodies at a time in accordance with the fifth embodiment of the present invention.

FIG. 10 shows the common dipping tank 11 which is sufficiently large to dip numerous solid electrolytic bodies 21 hung by the jig 19. Although FIG. 10 shows a total of four solid electrolytic bodies 21, the number of solid electrolytic bodies 21 to be dipped simultaneously can be arbitrarily changed.

Although not shown in the drawing, the jig 19 is equipped with a rotating mechanism for rotating each solid electrolytic body 21 about its central axis (refer to arrow 210).

When the solid electrolytic body 21 is dipped into the slurry 3 stored in dipping tank 11, the solid electrolytic body 21 rotates in the slurry 3.

The dipping tank 11 of FIG. 10 is the one disclosed in any one of the first to fourth embodiments of the present invention.

The rest of the arrangement is substantially the same as that of the first embodiment.

By rotating the solid electrolytic bodies 21 as shown in FIGS. 9 and 10, it becomes possible to form a uniform slurry film on the surface of the solid electrolytic body 21.

The effects and functions of the slurry tank 11 can be obtained in the same manner as in the first to fifth embodiments.

This invention may be embodied in several forms without departing from the spirit of essential characteristics thereof. The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A method for manufacturing a gas sensing element which has a cup-shaped solid electrolytic body having a reference gas chamber formed therein, an inside electrode provided on an inner surface of said solid electrolytic body, an outside electrode provided on an outer surface of the solid electrolytic body, and a porous layer formed so as to cover said outside electrode, said manufacturing method comprising:

a step of forming said solid electrolytic body;

a step of providing said inside electrode on a predetermined portion of said inner surface of said solid electrolytic body and providing said outside electrode on a predetermined portion of said outer surface of said solid electrolytic body; and a step of dipping said solid electrolytic body into a slurry which is prepared for forming said porous layer by using a dipping apparatus, wherein said dipping apparatus comprises:

a dipping tank for storing said slurry which is prepared for forming said porous layer, a viscosity adjusting tank equipped with a viscosity sensor for measuring a viscosity of said slurry and a viscosity adjusting mechanism for adjusting the viscosity of said slurry based on a sensing value of said viscosity sensor, a fluid passage for connecting said dipping tank and said viscosity adjusting tank, and a circulating pump provided in said fluid passage for forcibly circulating said slurry between said dipping tank and said viscosity adjusting tank, wherein said dipping step includes:

a step of dipping said solid electrolytic body into said slurry stored in said dipping tank while said slurry is forcibly circulated between said dipping tank and said viscosity adjusting tank by said circulating pump, a step of forming a slurry film on a predetermined portion of said solid electrolytic body through this dipping treatment, and a step of sintering said slurry film to form said porous layer.

2. The method for manufacturing a gas sensing element in accordance with claim 1, wherein said dipping tank has a fluid inlet port for introducing said slurry from said viscosity adjusting tank, a receiving groove is provided along an opening of said dipping tank so as to surround a circumferential upper end of said dipping tank to receive the slurry overflowed from said dipping tank, and a fluid outlet port provided in said receiving groove for discharging the overflowed slurry to said viscosity adjusting tank.

3. The method for manufacturing a gas sensing element in accordance with claim 1, wherein a baffle is provided in said dipping tank so as to be positioned adjacent to said fluid inlet port so that flow of the slurry introduced from said viscosity adjusting tank collides with said baffle.

4. The method for manufacturing a gas sensing element in accordance with claim 1, wherein a porous stirring plate is provided in said dipping tank, and said stirring plate oscillate in said dipping tank.

5. The method for manufacturing a gas sensing element in accordance with claim 1, further comprising a step of forming a ceramic protective layer on said solid electrolytic body before dipping said solid electrolytic body into said slurry.

6. The method for manufacturing a gas sensing element in accordance with claim 1, wherein said solid electrolytic body is rotated when said solid electrolytic body is dipped into said slurry.

7. The method for manufacturing a gas sensing element in accordance with claim 1, wherein said solid electrolytic body is stationary when said solid electrolytic body is dipped into said slurry.

8. A method for manufacturing a gas sensing element which has a cup-shaped solid electrolytic body having a reference gas chamber formed therein, an inside electrode provided on an inner surface of said solid electrolytic body, an outside electrode provided on an outer surface of the solid electrolytic body, and a porous layer formed so as to cover said outside electrode, said manufacturing method comprising:

a step of forming said solid electrolytic body;

a step of providing said inside electrode on a predetermined portion of said inner surface of said solid electrolytic body and providing said outside electrode on a predetermined portion of said outer surface of said solid electrolytic body; and a step of dipping said solid electrolytic body into a slurry which is prepared for forming said porous layer by using a dipping apparatus, wherein said dipping apparatus comprises:

a dipping tank for storing said slurry which is prepared for forming said porous layer, a first stirrer shiftable in a circumferential direction along an opening of said dipping tank to stir said slurry, and a second stirrer rotatable in the vicinity of a bottom of said dipping tank to stir said slurry, wherein said dipping step includes:

a step of dipping said solid electrolytic body into said slurry stored in said dipping tank, a step of forming a slurry film on a predetermined portion of said solid electrolytic body through this dipping treatment, and a step of sintering said slurry film to form said porous layer.

9. The method for manufacturing a gas sensing element in accordance with claim 8, wherein said first stirrer is a stirring rod provided in the vicinity of said opening of said dipping tank so as to be shiftable in the circumferential direction along an inner wall surface of said dipping tank, and said second stirrer is rotary vanes rotatable about a rotary shaft provided on the bottom of said dipping tank.

10. The method for manufacturing a gas sensing element in accordance with claim 8, further comprising a step of forming a ceramic protective layer on said solid electrolytic body before dipping said solid electrolytic body into said slurry.

11. The method for manufacturing a gas sensing element in accordance with claim 8, wherein said solid electrolytic body is rotated when said solid electrolytic body is dipped into said slurry.

12. The method for manufacturing a gas sensing element in accordance with claim 8, wherein said solid electrolytic body is stationary when said solid electrolytic body is dipped into said slurry.

* * * * *